United States Patent [19]
Naritomi et al.

[11] Patent Number: 6,132,998
[45] Date of Patent: *Oct. 17, 2000

[54] PROCESS FOR CONTINUOUSLY PREPARING BACTERIAL CELLULOSE

[75] Inventors: Takaaki Naritomi; Tohru Kouda; Michi Naritomi; Hisato Yano; Fumihiro Yoshinaga, all of Kawasaki, Japan

[73] Assignee: Bio-Polymer Research Co., Ltd., Kawasaki, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/981,495
[22] PCT Filed: May 21, 1997
[86] PCT No.: PCT/JP97/01713
  § 371 Date: Feb. 26, 1998
  § 102(e) Date: Feb. 26, 1998
[87] PCT Pub. No.: WO97/44477
  PCT Pub. Date: Nov. 27, 1997

[30] Foreign Application Priority Data

May 21, 1996 [JP] Japan ................................... 8-148487

[51] Int. Cl.[7] ............................ C12P 19/04; C12P 19/00; C08B 15/00
[52] U.S. Cl. .............................. 435/101; 435/72; 536/56; 536/126; 536/123.12
[58] Field of Search ....................... 435/101, 72; 536/56, 536/126, 123.12

[56] References Cited

PUBLICATIONS

Matsuoka et al, Biosci. Biotech. Biochem. 60(4): 575–579 (1996).
Toyosaki et al, J. Gen. Appl. Microbiol. 41:307–314 (1995).

*Primary Examiner*—Francisco Prats
*Attorney, Agent, or Firm*—Oblon, Spivak, McClelland, Maier & Neustadt, P.C.

[57] ABSTRACT

An object of the present invention is to obtain the high production rate and yield of BC. The present invention relates to a process for the production of cellulosic material at a production rate of 0.4 g/L/hr or more, which comprises culturing cellulose-producing bacteria while maintaining the concentration of the residual sugars in a culture broth at 20 g/L or less, and to a process for the production of cellulosic material at a production rate of 0.4 g/L/hr or more, which comprises culturing cellulose-producing bacteria in a culture medium containing a factor which improves an apparent affinity of substrate for sugars.

10 Claims, 3 Drawing Sheets

RELATIONSHIP AMONG THE DILUTION RATE, THE BC PRODUCTION RATE AND THE RESIDUAL FRUCTOSE IN THE DRAWN BROTH

RELATIONSHIP AMONG THE DILUTION RATE, THE YIELD AGAINST THE CONSUMED SUGARS AND THE YIELD AGAINST THE SUPPLIED SUGARS

CALCULATIONS OF AFFINITY CONSTANT OF FRUCTOSE BY LINEWEAVER-BURK PLOT IN CONTINUOUS CULTURES USING THREE DIFFERENT MEDIA

PROCESS FOR CONTINUOUSLY PREPARING BACTERIAL CELLULOSE

TECHNICAL FIELD

This invention relates to a process for the production of cellulosic material (bacterial cellulose: "BC") at a high rate, which comprises using microorganisms capable of producing BC (cellulose-producing bacteria) while maintaining the concentration of the residual sugars in a culture broth at a specific level or less.

BACKGROUND ART

Since BC is edible, it is utilized in the food industry. BC's high dispersibility in water further provides it with a lot of industrial applications, such as to maintain viscosity of food, cosmetics or coating agents, to strengthen food materials, to maintain moisture, to improve stability of food, and to be used as low-calorie additives and as an emulsion stabilizer.

BC is characterized by a sectional width of its fibrils, which is smaller by two orders of magnitude than that of other kinds of cellulose such as those derived from wood pulp.

Owing to such structural and physical features of microfibrils, a homogenized BC has plenty of industrial applications as a strengthening agent for polymers, especially hydrophilic polymers. Products prepared by solidification of the homogenized BC in the form of a lump or paper show a high elastic modulus in tension owing to the above feature, and are therefore expected to have excellent mechanical properties for use in various kinds of industrial materials.

Methods for the production of BC are described in, for example, Japanese Patent Laid-Open Application Sho 62(1987)-265990, Japanese Patent Laid-Open Application Sho 63(1988)-202394 and Japanese Patent Publication Hei 6(1994)-43443.

As a nutrient medium suitable for the cultivation of the cellulose-producing bacteria, Schramm/Hestrin medium is known, which contains carbon source, peptone, yeast extract, sodium phosphate and citric acid (Schramm et al., J. General Biology, 11,pp.123–129, 1954). Further, it has been found that the productivity of the BC is increased by the addition of an accelerator for the cellulose production such as inositol, phytic acid and pyrroloquinoline quinone (PQQ) (Japanese Patent Publication Hei 5(1993)-1718; Mitsuo TAKAI, Japan TAPPI Journal, Vol.42, No.3, pp.237–244), carboxylic acid or their salts (Japanese Patent Laid-Open Application Hei 5(1993)-191467; Japanese Patent Laid-Open Application Hei 7(1995)-39386), invertase (Japanese Patent Application Hei 5(1993)-331491; Japanese Patent Laid-Open Application Hei 7(1995)-184677) and methionine (Japanese Patent Application Hei 5(1993)-335764; Japanese Patent Laid-Open Application Hei 7(1995)-184675) into such a nutrient medium.

Furthermore, there have been proposed a method for cultivating the cellulose-producing bacteria under a specific range of oxygen-transfer coefficient ($K_L a$) (Japanese Patent Application Hei 7(1995)-31787), a method for cultivating the cellulose-producing bacteria while maintaining the concentration of carbon sources in a culture broth at a specific level or more (Japanese Patent Application Hei 7(1995)-267407) and a method for cultivating the cellulose-producing bacteria while maintaining the internal pressure within a fermentation tank at a specific level or more at a certain stage during the cultivation (Japanese Patent Application Hei 7(1995)-76408).

The bacteria may be generally cultured in any known culture conditions such as static culture, shaken culture, and aerated and agitated culture, and in any known culture operation methods such as batch fermentation, fed batch fermentation, repeated batch fermentation and continuous fermentation.

Means for agitation include impellers (agitating blades), air-lift fermenters, pump-driven recirculation of the fermenter broth and any combination of these means.

The impellers include gate-shape impellers, turbine impellers, double helical ribbon impellers and screw impellers.

An economical and high-yielding method for the production of bacterial cellulose is described in Japanese Patent Laid-Open Application Hei 8(1996)-33495, wherein the concentration of the bacterial cellulose in a culture medium is kept at a specific level or less or the oxygen consumption rate is kept at a specific level or more by a continuous removal of the culture medium from its culture system and a continuous supply of a fresh culture medium having almost the same volume as the removed culture broth.

The above method has overcome the disadvantages that accumulation of BC in the culture broth during the culture of the cellulose-producing bacteria will increase viscosity of the culture broth and make it difficult to supply a necessary amount of oxygen into the culture broth. As a result, a high production rate has been attained. However, since a dilution rate (i.e., a rate of supply of the medium) is relatively high, sugars will remain unused in the withdrawn culture broth, leaving a problem to be solved in the yield of BC production.

The present inventors have studied to solve the above problem so as to make the present invention.

DISCLOSURE OF INVENTION

The present invention relates to a process for the production of cellulosic material at a production rate of 0.4 g/L/hr or more, which comprises culturing cellulose-producing bacteria while maintaining the concentration of the residual sugars in a culture broth at 20 g/L or less, preferably at 8 g/L or less.

In the present method, the culture broth containing BC is continuously drawn from its culture system while maintaining the concentration of the residual sugars in the culture broth by controlling the dilution rate. As a result, BC yield may be increased in the continuous cultivation of cellulose-producing bacteria.

The term "continuous" in the present specification also contains the meaning of "intermittent" or "off and on." Thus, this concept includes not only an embodiemnt wherein the supply of the culture medium and withdrawing of the culture broth in its culture system is successively carried out at a constant flow rate by means of a peristatic pump and the like, but also an embodiment wherein the supply of the culture medium and withdrawing of the culture broth is carried out at a certain interval.

In any case, the concentration of the residual sugars in the culture broth may be maintained at a low level by determining the amount of supply and withdrawing depending on a monitored value of the concentration of the residual sugars in the withdrawn culture broth.

One example of maintaining the concentration of the residual sugars in the culture broth at 20 g/L or less may be to control the dilution rate at 0.12/hr or less in the case of using BPR 3001A strain as the cellulose-producing bacteria.

The "dilution rate" is defined as follows in the present specification:

$$D=F/V$$

wherein

D: Dilution rate (/hr),

F: Supply rate of the culture medium and

V: Amount of the culture broth within a fermentation tank.

Further, the present invention relates to a method for the production of cellulosic material, which comprises culturing cellulose-producing bacteria in a culture medium containing a factor which improves an apparent affinity of bacteria for sugars substrate such as fructose or decreases an affinity constant of substrate (Ks).

The factor includes lactic acid, ethanol, acetaldehyde, acetic acid, pyruvic acid and glycerol as well as the combination thereof.

The concentration of the factors in the medium may be optionally determined by those skilled in the art considering culturing conditions such as the kinds of bacteria to be cultured and culture medium and the like, being usually in the range of 1–30 g/L.

The "affinity constant of substrate (Ks)" means the affinity between the bacteria and a substrate, and is equal to the value of the concentration of the substrate when "half the maximum value of a specific growth rate ($\mu_{max}$)" is shown. Thus, the higher the affinity of substrate for a certain substrate is, the smaller the value of affinity constant of substrate (Ks) becomes. According to Monod's equation, the following relation is found among the affinity constant of substrate (Ks), the maximum value of a specific growth rate ($\mu_{max}$), a specific growth rate ($\mu$) and the concentration of the remaining substrates (S):

$$\mu=\mu_{max}S/(Ks+S)$$

Since the dilution rate (D) may be considered to be equal to the specific growth rate ($\mu$) at a steady state in the continuous cultivation, the value of the affinity constant of substrate (Ks) of a particular bacterium will be empirically calculated by means of Lineweaver-Burk plot for a given substrate, based on the relationship between the concentration of the substrate in the culture broth and dilution rate at the steady state.

In addition to the above culture conditions and culture operation methods, it is also possible to use for the present invention the method for the production of BC described in the Japanese Patent Application Hei 6(1994)-192287 (Japanese Patent Laid-Open Application Hei 8(1996)-33494), wherein a culture broth containing bacteria is circulated between a cultivating apparatus and a separator such as a floatation equipment and an edge filter to separate the resulting BC from the bacteria and culture broth in said separator.

The cellulose-producing bacteria used in the present invention include Acetobacter strains such as *Acetobacter xylinum* subsp. *sucrofermentans* such as BPR 2001 strain, *Acetobacter xylinum* ATCC23768, *Acetobacter xylinum* ATCC23769, *Acetobacter pasteurianus* ATCC10245, *Acetobacter xylinum* ATCC14851, *Acetobacter xylinum* ATCC11142, *Acetobacter xylinum* ATCC10821; Agrobacterium; Rhizobium; Sarcina; Pseudomonus, Achromobacter; Alcaligenes; Aerobacter; Azotobacter; and Zooglea; and strains derived from those strains by using known mutagens such as NTG (nitrosoguanidine).

The BPR 2001 was deposited at the National Institute of Bioscience and Human-Technology, Agency of Industrial Science and Technology (1–3, Higashi 1-chome, Tsukuba-shi, Ibaraki-ken 305 Japan) on Feb. 24, 1993 under accession number FERM P-13466, and then transferred on Feb. 7, 1994 to the deposit under the terms of the Budapest Treaty on the International Recognition of the Deposit of Microorganisms for the Purposes of Patent Procedure and Regulation under accession number FERM BP-4545.

The chemical treatment using mutagens such as NTG is described in, for example, Bio Factors, Vol. 1, pp.297–302 (1988) and J. Gen. Microbiol, Vol. 135, pp.2917–2929 (1989). Accordingly, those skilled in the art may obtain the present mutants in accordance with these known methods. The present mutants may be also obtained by other treatments such as application of radioactive rays.

Among the thus obtained mutants, it is preferred to use cellulose-producing bacteria capable of producing a bacterial cellulose having a weight-average degree of polymerization (in terms of polystyrene) of $1.6 \times 10^4$ or above, preferably of $1.7 \times 10^4$ or above in an aerobic agitated culture, or cellulose-producing bacteria capable of producing a bacterial cellulose having a weight-average degree of polymerization (in terms of polystyrene) of $2.0 \times 10^4$ or above in a static culture.

One example of the present cellulose-producing bacteria, BPR3001A, has been deposited at the National Institute of Bioscience and Human-Technology, Agency of Industrial Science and Technology (1–3, Higashi 1-chome, Tsukuba-shi, Ibaraki-ken 305 Japan) on Jun. 12, 1995 under accession number FERM P-14982, and then transferred on Feb. 23, 1996 to the deposit under the terms of the Budapest Treaty on the International Recognition of the Deposit of Microorganisms for the Purposes of Patent Procedure and Regulation under accession number FERM BP-5421.

It is well known that strength and elasticity of polymeric materials are improved as their degree of polymerization increases. As that is also the case with a bacterial cellulose, membranes prepared from bacterial cellulose having a high degree of polymerization will show higher strength and elasticity than membranes prepared from bacterial cellulose having a relatively low degree of polymerization. Accordingly, by using the bacterial cellulose with a high degree of polymerization, the membrane with a high strength and elasticity may be obtained in the present invention.

The weight-average degree of polymerization of a variety kinds of cellulose such as BC of this invention may be determined by the method using a GPC system (Tosoh HLC-8020) equipped with an RI detector as follows:

A cellulose sample is nitrated with a fuming nitric acid-phosphorous pentaoxide solution according to the method of W. J. Alexander, R. L. Mitchell, Analytical Chemistry 21, 12, 1497–1500 (1949).

Nitrated cotton linter is used as a control.

Nitrated cellulose is then dissolved in THF (Wako Pure Chemical Industries Ltd., the first grade) to a final concentration of 0.05%, and filtered through a 1.0 $\mu$m pore-size filter. THF is also used for an elution solvent.

The flow rate, pressure, and sample-injection volume are adjusted to be 0.5 ml/min., 10–13 kgf/cm$^2$ and 100 $\mu$l, respectively.

The column system consists of two TSKgel GMH-HR (S) columns (7.5 ID×300 mm) and a guard column (Tosoh Co., Ltd.). The analysis is carried out at a temperature of 35° C.

A relative molecular weight in terms of polystyrene is calculated by using polystyrene standards (Tosoh).

The polystyrene standards having a molecular weight in the range of $2.0 \times 10^7$ to 2630 are used and a standard curve is prepared based on the following three-dimension approximate equation:

$$\log M = At^3 + Bt^2 + Ct + D$$

wherein "t" is an elution time and "M" is a molecular weight.

The weight-average molecular weight and number-average molecular weight are calculated by a program (ver. 3, 10) equipped in a data processor (SC-8020).

The weight-average degree of polymerization and number-average degree of polymerization of the original cellulose samples are finally calculated based on the above data, taking substitution degrees after the nitration into consideration.

Carbon sources in the culture media useful in the present invention include sucrose, glucose, fructose, mannitol, sorbitol, galactose, maltose, erythritol, glycerol, ethyleneglycol, ethanol and their mixtures. In addition, sucrose may be combined with starch hydrolysate containing these carbon sources, citrus molasses, beet molasses, squeezed juice from beet or sugar cane, juice from citrus and the like.

Nitrogen sources useful in the present invention include organic or inorganic substances such as ammonium salts including ammonium sulfate, ammonium chloride, ammonium phosphate; nitrates; and urea. Nitrogen-containing natural nutrients may be also used including Bacto-Peptone, Bacto-soytone, Yeast-Extract, and Bean-Condensate.

A trace amount of organic nutrients may be further added including amino acids, vitamins, fatty acids, nucleic acids, 2,7,9-tricarboxy-1H pyrrolo[2,3,5]-quinoline-4,5-dione, sulfite pulp waste liquor, lignin sulfonic acid and the like.

When the mutants with nutritional requirement for amino acids are used, such required nutrients should be supplemented in the culture media. Inorganic nutrients include phosphate salts, magnesium salts, calcium salts, iron salts, manganese salts, cobalt salts, molybdate salts, hematite salts, chelate metal salts and the like.

It is also possible to optionally supply the abovementioned accelerators for the cellulose production.

For example, when the Acetobacter is used as the cellulose-producing bacteria, a pH range for the culture is controlled between 3 and 7, preferably around 5. A culture temperature is kept in a range between 10 and 40° C., preferably between 25 and 35° C. Oxygen supply into a cultivating apparatus may contain from 1 to 100% oxygen, desirably 21 to 80%. Those skilled in the art may optionally determine the contents of these components in the culture media and the inoculation of the bacteria into the media, depending on the culture method to be used.

The BC produced in the present method may be recovered together with the bacterial cells, and then impurities other than the BC, including the bacterial cells per se, may be removed from the recovered BC.

The impurities may be almost completely removed from the BC by washing, dehydration under pressure, dilute acid washing, alkali washing, bleaching with hypochlorite soda or hydrogen peroxide, lysing with lytic enzymes such as lysozyme, treatment with surfactants such as lauryl sulfate soda or deoxycholate soda, washing under heat at a temperature range between a room temperature and 200° C., and any combination of these treatments.

The BC thus obtained according to the present invention includes cellulose, those comprising heteropolysugars having cellulosic main chains, and those comprising β-1,3- or β-1,2-glucan. Said heteropolysugars contain as components hexoses, pentoses and organic acids such as mannose, fructose, galactose, xylose, arabinose, rhamnose and glucuronic acid, as well as glucose.

These polysugars may be present alone or as a mixture combined each other via hydrogen bonds.

BEST MODE FOR CARRYING OUT THE INVENTION

Figure 1:
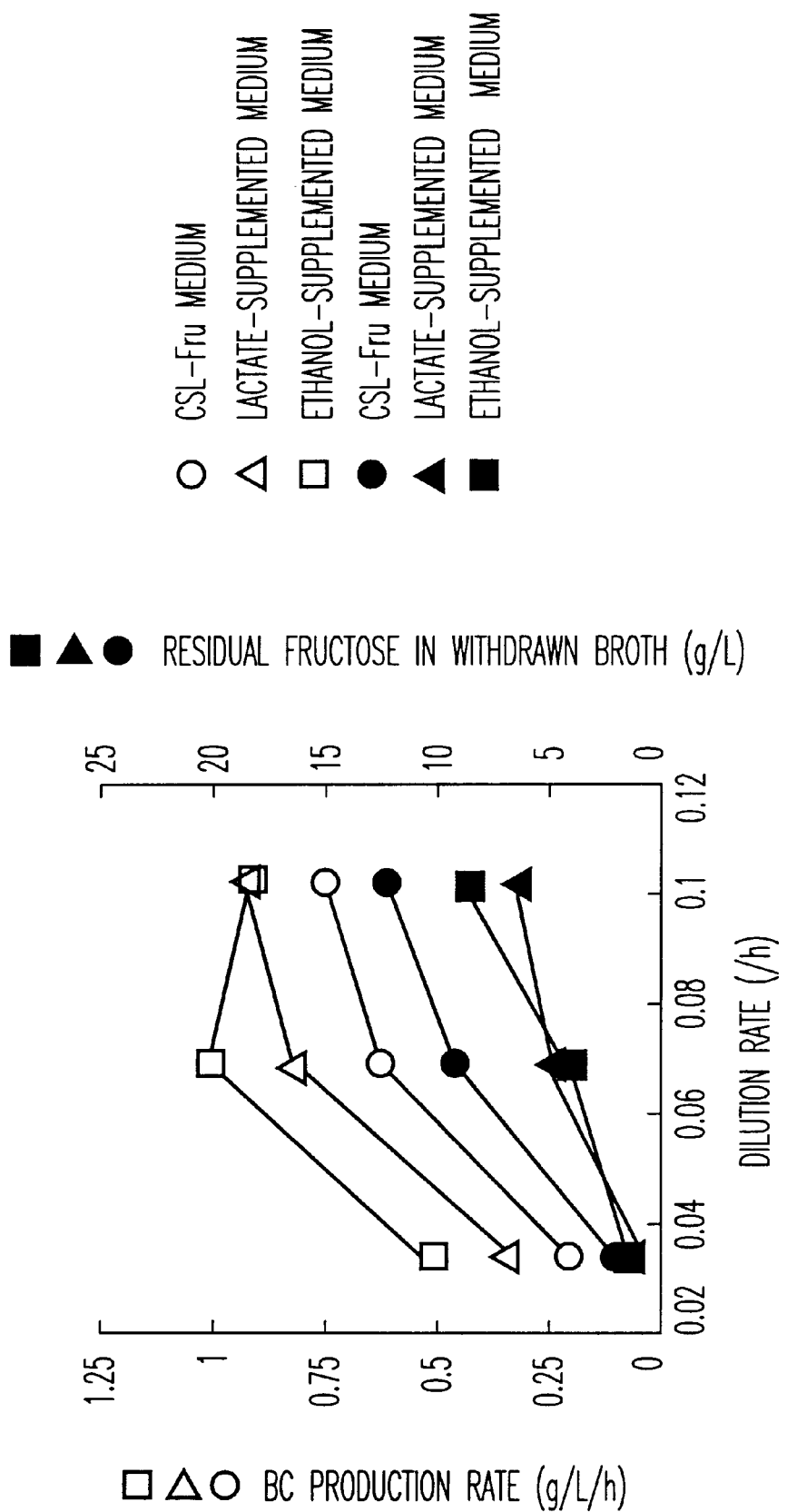
FIG. 1 shows the relationship among the dilution rate, the production rate of BC and the concentration of the residual sugars in the drawn broth.

The present invention will be further illustrated according to the following examples.

EXAMPLE 1

BPR 3001A strain was continuously cultured under the following conditions.
Cultivating Condition A conical flask with slanted baffles (500 ml volume) containing 112.5 ml of CSL-Fru medium shown in Table 1 was inoculated with a Roux flask culture mixture (12.5 ml), and incubated for three days at 28° C. with shaking at 180 rpm. The resulting culture mixture was aseptically homogenized with a homogenizer for 1 min at 10,000 rpm. 12.5 ml of the thus homogenized culture mixture was divided and inoculated into six conical flasks with slanted baffles (500 ml volume each) containing 112.5 ml each of CSL-Fru medium shown in Table 1 and cultured for 24 hours at 28° C. with shaking at 180 rpm.

The resulting culture mixture (160 ml) was then inoculated into each of three jars (3L volume each) containing 1440 ml each of CSL-Fru medium shown in Table 1 and subjected to a batch fermentation. The starting concentrations of sugars and CSL were 40 g/L and 4 v/v %, respectively. A pH range for the culture is controlled at 5+0.1 and a culture temperature is kept at 30° C. An amount of aeration was maintained at 800 ml/min, and a rate of agitation was kept in the range between 200 and 1200 rpm so that an amount of dissolved oxygen could be satisfied.

The following three kinds of culture media were used:
(1) CSL-Fru medium shown in FIG. 1 with an exception of the concentration of the sugars of 30 g/L;
(2) The above medium in (1) further supplemented with 7.5 g/L of lactic acid; and
(3) The above medium in (1) further supplemented with 10 g/L of ethanol.

During the BC production, each of the above three media was supplied for 36 hours at the dilution rate of 0.034 (/hr), 0.069 (/hr) 0.102 (/hr), respectively, after 20 hours had passed since the initiation of culture. The amounts of the supplied culture medium and withdrawn culture broth were weighed and controlled so as to be the same with each other.

Figure 2:
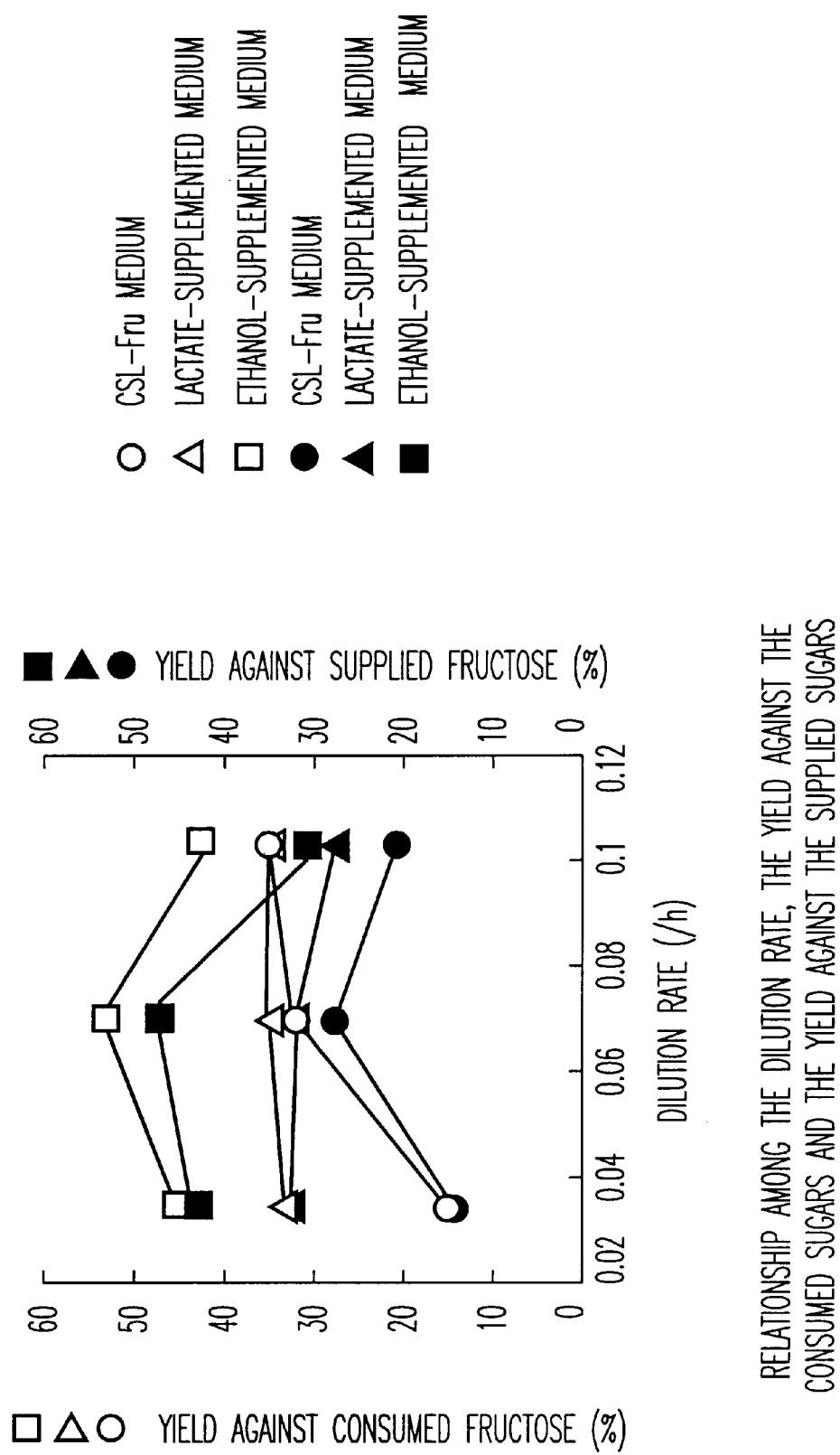
FIG. 2 shows the relationship among the dilution rate, the yield against the consumed sugars and the yield against the supplied sugars.

The resulting relationship among the dilution rate, the production rate of BC and the concentration of the residual sugars in the withdrawn broth, and the relationship among the dilution rate, the yield against the consumed sugars and the yield against the supplied sugars are shown in FIG. 1 and FIG. 2, respectively.

TABLE 1

CSL-Fru medium

| Fructose | 4.0 (%) |
|---|---|
| $KH_2PO_4$ | 0.1 |
| $MgSO_4 \cdot 7H_2O$ | 0.025 |
| $(NH_4)_2SO_4$ | 0.33 |
| Vitamin Mixture (see below) | 1.0 |
| Salt Mixture (see below) | 1.0 |
| CSL (Corn Steep Liquor) | 4.0 |
| pH | 5.0 |

TABLE 2

Vitamin Mixture

| compound | mg/L |
|---|---|
| Inositol | 200 |
| Niacin | 40 |
| Pyridoxine HCl | 40 |
| Thiamine HCl | 40 |
| Ca Pantothenate | 20 |
| Riboflavin | 20 |
| p-Aminobenzonic Acid | 20 |
| Folic Acid | 0.2 |
| Biotin | 0.2 |

TABLE 3

Salt Mixture

| $FeSO_4 \cdot 7H_2O$ | 360(mg/L) |
|---|---|
| $CaCl_2 \cdot 2H_2O$ | 1470 |
| $Na_2MoO_2 \cdot 2H_2O$ | 242 |
| $ZnSO_4 \cdot 7H_2O$ | 173 |
| $MnSO_4 \cdot 5H_2O$ | 139 |
| $CuSO_4 \cdot 5H_2O$ | 5 |

The concentration of the residual sugars in the withdrawn culture broth was determined by subjecting a sample of the withdrawn culture broth appropriately diluted and filtered through cellulose acetate membrane of 0.45 μm to high performance liquid chromatography (Nihon Bunko Co., Ltd. HPLC separation column: Shodex Asahipak NH2P-50 4E).

The accumulated amount of BC (g/L) was calculated for obtaining the production rate of BC in the continuous cultivation as follows. The solid contents in the withdrawn culture broth were collected, washed with water to remove the medium components, and treated with 1 N NaOH aqueous solution at 80° C. for 20 minutes to remove the bacterial cells. The resulting cellulose was washed until the washing water became approximately neutral, and dried under vacuum at 80° C. for 12 hours to weigh the dry cellulose.

The yield against the consumed sugars (%) and the yield against the supplied sugars (%) were calculated as follows. Calculation of Yield Aaganist the Consumed Sugars (%)

In the continuous cultivation system wherein a culture medium having the concentration of sugars ($Fru_{in}$ (g/L)) is supplied at the rate of supply (F(L/hr)), there is the culture broth of V (L) having the concentration of BC ($BC_0$ (g/L)) and the concentration of sugars ($Fru_0$ (g/L)) at the time of $t_0$. Then at the time of $t_1$, the concentration of BC and the concentration of sugars have changed to ($BC_1$ (g/L)) and ($Fru_1$ (g/L)), respectively. During the time course from $t_0$ to $t_1$, v (L) of the culture broth was withdrawn, wherein the concentration of BC is $BC_{out}$ (g/L) and the concentration of the residual sugars is $Fru_{out}$ (g/L).

The yield against the consumed sugars Yc (%) is represented as follows:

$$Yc = (P_1 - P_0 + P_{out})/(S_0 + S_{in} - S_1 - S_{out}) * 100$$

wherein

Yc: Yield against the consumed sugars (%)

$P_0$: Total amount of BC in the fermenter at $t_0$ (g) ($P_0 = BC_0 * V$)

$P_1$: Total amount of BC in the fermenter at $t_1$ (g) ($P_1 = BC_1 * V$)

$P_{out}$: Total amount of BC in the culture broth withdrawn during the time from $t_0$ to $t_1$ (g) ($P_{out} = BC_{out} * V$)

$S_0$: Total amount of sugars in the fermenter at $t_0$ (g) ($S_0 = Fru_0 * V$)

$S_1$: Total amount of sugars in the fermenter at $t_1$ (g) ($S_1 = Fru_1 * V$)

$S_{in}$: Total amount of sugars supplied from $t_0$ to $t_1$ (g) ($S_{in} = Fru_{in} * v$)

$S_{out}$: Total amount of sugars in the culture broth withdrawn during the time from $t_0$ to $t_1$ (g) ($S_{out} = Fru_{out} * v$)

t: Course of time (hr) ($t = t_1 - t_0$)

v: Amount of the culture broth withdrawn during the time from to $t_0$ $t_1$ (v = F*t)

Calculation of Yield Against the Supplied Sugars (%)

The yield against the supplied sugars Yt (%) is represented as follows:

$$Yt = (P_1 - P_0 + P_{out})/S_{in} * 100$$

wherein

Yt: Yield against the supplied sugars (%)

$P_0$: Total amount of BC in the fermenter at $t_0$ (g) ($P_0 = BC_0 * V$)

$P_0$: Total amount of BC in the fermenter at $t_1$ (g) ($P_1 = BC_1 * V$)

$P_{out}$: Total amount of BC in the culture broth withdrawn during the time from $t_0$ to $t_1$ (g) ($P_{out} = BC_{out} * v$)

$S_{in}$: Total amount of sugars supplied from $t_0$ to $t_1$ (g) ($S_{in} = Fru_{in} * v$)

t: Course of time (hr) ($t = t_1 - t_0$)

v: Amount of the culture broth withdrawn during the time from $t_0$ to $t_1$ (v = F*t)

REFERENCE EXAMPLE

The relationship between the dilution rate (D) and the concentration of the residual sugars in the withdrawn culture broth (S) was studied at the steady state of the continuous cultivation using the three different supplying culture media.

Figure 3:
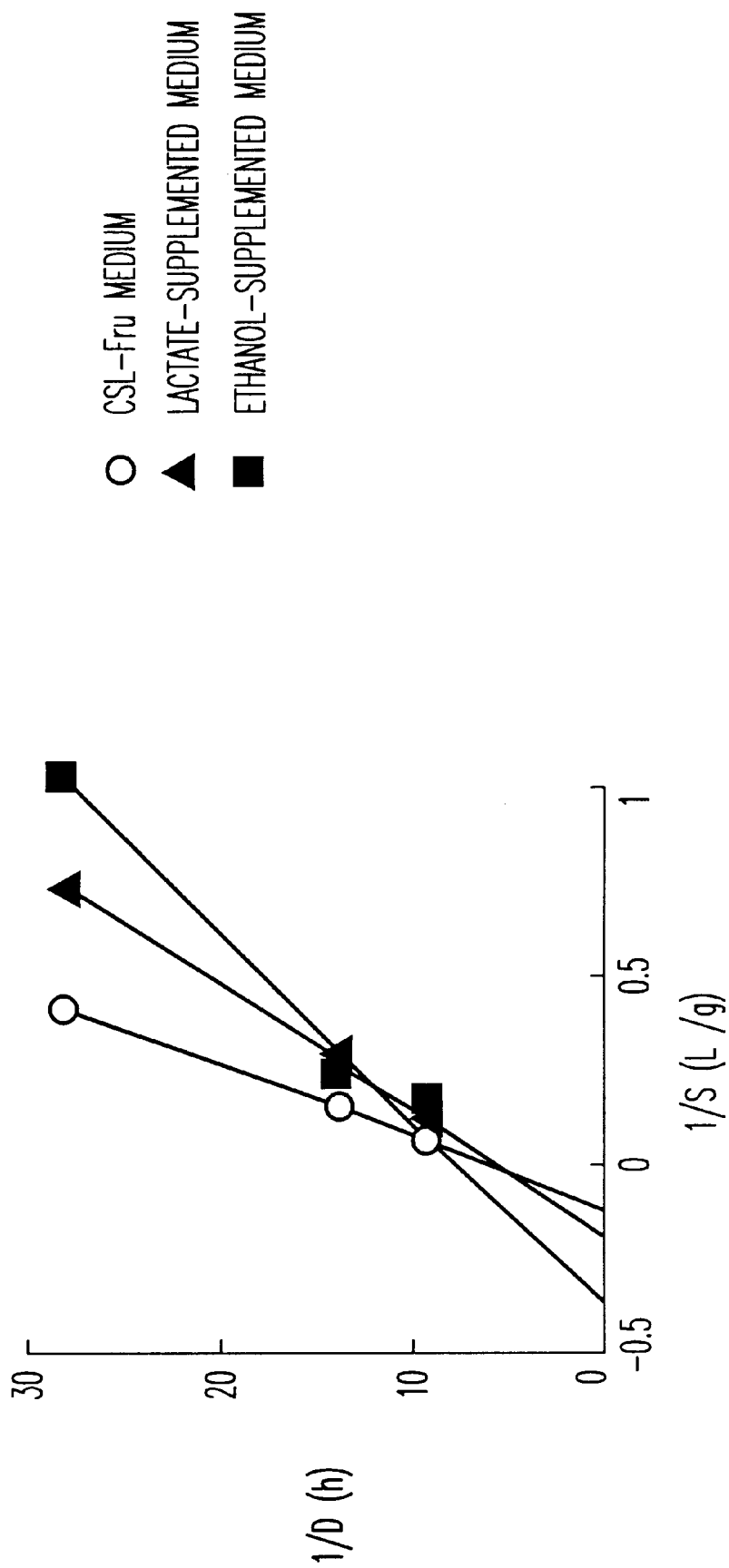
FIG. 3 plots reciprocal numbers (1/S) and (1/D) of the concentration of the residual substrates (sugars) (S) and the concentration of the dilution rate (D), repectively.

According to the following modified Monod's equation, the reciprocal numbers (1/S) and (1/D) of the concentration of the residual substrates (sugars) (S) and the concentration of the dilution rate (D), repectively, are plotted in FIG. 3.

$$1/\mu = 1/D = (Ks/\mu_{max}) * (1/S) + (1/\mu_{max})$$

Segment in the X-axis obtained by the method of least squares in the above analysis was equal to (-1/Ks). The results are shown in Table 4.

Table 4 demonstrates that the addition of ethanol or lactic acid reduces the value of the affinity constant of substrate (Ks), meaning the improvement of an apparent affinity for sugars.

TABLE 4

Apparent value of the constant of affinity (Ks) of
BPR 3001A strain for fructose in the continuous cultivation

| Medium | Constant of affinity of substrate (Ks) |
|---|---|
| CSL-Fru (control) | 9 (g/L) |
| CSL-Fru plus Ethanol | 5.6 |
| CSL-Fru plus Lactic acid | 3.3 |

INDUSTRIAL APPLICABILITY

As seen form the results shown in FIG. 1, by the addition of the factor such as ethanol or lactic acid which improves an apparent affinity of substrate of the bacteria for sugars in the culture broth according to the present invention, the advantages may be effected that the production rate of BC is increased while the concentration of the residual sugars in the drawn culture broth is decreased at the same dilution rate in the continuous cultivation of the cellulose-producing bacteria, when compared with the case using as the control CSL-Fru medium containing no such factors.

FIG. 2 shows that the above addition may further improve both the yield against the consumed sugars and yield against the supplied sugars.

What is claimed is:

1. A process for the production of cellulosic material at a production rate of 0.4 g/L/hr or more in a culture system, which comprises:

continuously culturing cellulose-producing bacteria while continuously removing culture medium from the system containing the culture medium and continuously supplying fresh culture medium thereto such that the concentration of sugars in the withdrawn culture medium in said system is maintained at no more than 20 g/L.

2. The process of claim 1, wherein the concentration of sugars in the culture broth is 8 g/L or less.

3. The process of claim 1, wherein said cellulose-producing bacteria are selected from the group consisting of genera of Acetobacter, Agrobacterium, Rhizobium, Sarcina, Pseudomonous, Achromobacter, Alcaligenes, Aerobacter, Azotobacter, Zooglea and strains derived from these bacterial strains employing known mutagens.

4. The process of claim 1, wherein said cellulosic material has a weight average degree of polymerization of $1.6 \times 10^4$ or above.

5. A process for the production of cellulosic material at a production rate of 0.4 g/L/hr or more in a culture system, which comprises:

continuously culturing cellulose-producing bacteria while continuously removing culture medium from the system containing the culture medium and continuously supplying fresh culture medium thereto such that the culture medium contains a factor which increases the affinity of said bacteria to substrate thereby decreasing substrate affinity constant (Ks).

6. The process for the production of cellulosic material according to claim 5, wherein the factor is selected from the group consisting of lactic acid, ethanol, acetaldehyde, acetic acid, pyruvic acid, glycerol and combinations thereof.

7. The process according to claim 6, wherein said factor is present in the culture medium in a concentration ranging from 7.5 to 30 g/L.

8. The process according to claim 5, wherein said factor is present in the culture medium in a concentration ranging from 7.5 to 30 g/L.

9. The process according to claim 5, wherein said cellulose-producing bacteria are selected from the group consisting of genera of Acetobacter, Agrobacterium, Rhizobium, Sarcina, Pseudomonous, Achromobacter, Alcaligenes, Aerobacter, Azotobacter, Zooglea and strains derived from these bacterial strains employing known mutagens.

10. The process of claim 5, wherein said cellulosic material has a weight average degree of polymerization of $1.6 \times 10^4$ or above.

* * * * *